United States Patent [19]
Green

[11] Patent Number: 5,203,773
[45] Date of Patent: Apr. 20, 1993

[54] TISSUE GRIPPING APPARATUS FOR USE WITH A CANNULA OR TROCAR ASSEMBLY

[75] Inventor: David T. Green, Westport, Conn.

[73] Assignee: United States Surgical Corporation, Norwalk, Conn.

[21] Appl. No.: 781,063

[22] Filed: Oct. 18, 1991

[51] Int. Cl.⁵ .................................................. A61M 29/00
[52] U.S. Cl. .................................... 604/104; 604/105
[58] Field of Search ............... 604/105, 104, 51, 52, 604/53, 54, 164, 175, 106, 107; 128/4

[56] References Cited

U.S. PATENT DOCUMENTS

| | | |
|---|---|---|
| 318,535 | 5/1885 | Bihler . |
| 365,969 | 7/1887 | Collins . |
| 504,424 | 9/1893 | De Pezzer . |
| 781,763 | 2/1905 | Bowker . |
| 1,621,159 | 3/1927 | Evans . |
| 1,719,428 | 7/1929 | Friedman . |
| 1,828,986 | 10/1931 | Stevens . |
| 1,863,057 | 6/1932 | Innes . |
| 1,870,942 | 8/1932 | Beatty . |
| 2,556,783 | 6/1951 | Wallace . |
| 2,649,092 | 8/1953 | Wallace . |
| 3,108,595 | 10/1963 | Overment . |
| 3,241,554 | 3/1966 | Coanda . |
| 3,261,357 | 7/1966 | Roberts et al. . |
| 3,344,791 | 10/1967 | Foderick . |
| 3,397,699 | 8/1968 | Kohl .................................... 604/105 |
| 3,692,029 | 9/1972 | Adair . |
| 3,713,447 | 1/1973 | Adair . |
| 3,938,530 | 2/1976 | Santomieri . |
| 3,946,741 | 3/1976 | Adair . |
| 4,043,338 | 8/1977 | Homm et al. . |
| 4,154,242 | 5/1979 | Termanini . |
| 4,228,802 | 10/1980 | Trott . |
| 4,250,873 | 2/1981 | Bonnet . |
| 4,389,208 | 6/1983 | LeVeen et al. . |
| 4,393,873 | 7/1983 | Nawash et al. . |
| 4,521,938 | 6/1985 | Kupcikevicius . |
| 4,571,241 | 2/1986 | Christopher . |
| 4,608,965 | 9/1986 | Anspach, Jr. et al. .................. 128/4 |
| 4,627,838 | 12/1986 | Cross et al. .......................... 604/105 |
| 4,648,383 | 3/1987 | Angelchik . |
| 4,648,402 | 3/1987 | Santos . |
| 4,660,571 | 4/1987 | Hess et al. . |
| 4,666,433 | 5/1987 | Parks . |
| 4,758,219 | 7/1988 | Sacks et al. .......................... 604/105 |
| 4,921,484 | 5/1990 | Hillstead . |
| 4,973,301 | 11/1990 | Nissenkorn . |
| 4,973,305 | 11/1990 | Goltzer . |
| 4,986,810 | 1/1991 | Semrad . |
| 4,995,868 | 2/1991 | Brazier . |
| 5,002,560 | 3/1991 | Machold et al. . |
| 5,122,122 | 6/1992 | Allgood . |

OTHER PUBLICATIONS

Dexide, Inc. Locking Trocar Advertisement, "Surgical Laparoscopy & Endoscopy" vol. 1, No. 4, Dec. 1991.
Dexide Advertisement-Monoscopy TM brand Locking Trocar with Woodford Spike TM.

*Primary Examiner*—John D. Yasko
*Attorney, Agent, or Firm*—Thomas R. Bremer; Peter G. Dilworth; Rocco S. Barrese

[57] ABSTRACT

A tissue gripping apparatus including a cylindrical member positioned about a tubular body portion or cannula. The cylindrical member includes a plurality of articulated arms that are movable between engageable and non-engageable positions. A hinge in the articulated arm enhances the tissue gripping abilities of the apparatus.

33 Claims, 2 Drawing Sheets

TISSUE GRIPPING APPARATUS FOR USE WITH A CANNULA OR TROCAR ASSEMBLY

BACKGROUND OF THE INVENTION

1. Field of the Invention

The present invention relates to surgical instruments for performing laparoscopic and endoscopic surgical procedures, and more particularly to a device for securing instruments such as cannulas in an incision in a patient's body during the surgical procedure.

2. Discussion of the Prior Art

In recent years, laparoscopic and endoscopic surgical procedures have become increasingly popular for performing major surgical operations. In such a procedure, a small incision or puncture is made in the patient's body to provide access for a tube or a cannula device. The tube or cannula device is inserted into the patient's body to allow for the insertion of instruments used in performing the surgical procedure, as well as for the insertion of a camera or endoscope to view the surgical objective.

Typically, a trocar device including, for example, an obturator and a cannula is employed to puncture the skin and provide access to the surgical area. A pointed obturator may be used for penetrating the skin to extend the trocar beyond the body wall to the surgical site. Alternatively, an incision may be made using a scalpel or similar device before inserting a blunt obturator through the incision. When either obturator is removed, the cannula remains in place to maintain access to the surgical site, and several incisions may be made to provide numerous access ports to the surgical objective. Once the cannulas are in place, various surgical instruments such as scissors, dissectors, retractors or the like, may be inserted by a surgeon to perform the surgery. Typically, a scope device is used to view the area directly, or a miniature camera is used to display the surgical site on a video monitor in the operating room.

The primary benefit of such minimally invasive surgical techniques is the reduction of scarring, and consequently, minimizing damage to surrounding tissue and organs. As a result, recovery time is greatly reduced for the patient.

During a laparoscopic surgical procedure, gas is introduced into the body cavity, usually the abdomen, by means of a pneumoperitoneum needle. The gas inflates the abdominal cavity to provide greater access to the surgical area and minimize obstruction during surgery. The trocar assembly is then inserted into the body cavity to a point adjacent the tissue or organ which is the surgical objective. Due to the gas insufflation, it is necessary to maintain a desired gas seal at each of the cannulas in position in the body. After the obturator is removed from the trocar assembly, the cannula remains in place in the patient's body. Ordinarily, a flapper valve in a housing at the proximal end of the cannula prevents the insufflation gas from escaping through the cannula after the obturator is removed. It is also preferred to maintain the cannulas in a relatively stable state, primarily to free the surgeon and the surgical assistants from having to hold the cannulas to prevent these instruments from backing off and consequently being displaced from the incision. Furthermore, the routine movement of the cannulas during the surgical procedure may result in a loss of gas tightness about the cannula, thereby negatively effecting the surgical procedure.

In order to support the cannula in a hands-off manner, and maintain the integrity of the gas seal at the incision, it has been known to provide various mechanisms and devices which attempt to maintain and secure the cannula in the incision.

Typical devices include penetration limiting devices such as the sleeve or collar disclosed in U.S. Pat. No. 3,817,251 to Hasson, which provides a conical sleeve which may be adjusted to various positions on the cannula to limit insertion of the cannula to specific depths. U.S. Pat. No. 4,077,412 to Moossun, U.S. Pat. No. 4,637,814 to Leiboff, as well as U.S. Pat. No. 4,627,838 to Cross et al., disclose devices to prevent the inadvertent removal or backing off of the cannula during the surgical procedure. Moossun provides an inflatable diaphragm member which is inflated once the cannula is positioned in the body cavity to prevent inadvertent removal of the cannula from the incision until the diaphragm is deflated. Leiboff also discloses an inflatable cuff member which is inflated in a body cavity to secure the device and seal the cavity at the opening to prevent leakage of irrigating fluid during an irrigation procedure. Cross et al. provide a complex wing-type mechanism which is extended once the catheter is positioned within the body cavity so that the wing members engage the body wall to prevent removal of the catheter until the wing mechanism is collapsed. These devices often require additional equipment to be present in the operating room, such as a gas or compressed air source to inflate the device.

Also known are sleeve members having external ribs which fit over a cannula. The sleeve is forced into the incision either by twisting or simply by forcing the sleeve into the incision along with the catheter. Further, devices are known that include a "Malecott" type wing arrangement such as U.S. Pat. 4,608,965 to Anspach, Jr. et al. Anspach discloses an endoscopic retainer and tissue retracting device including a cylindrical tube having flexible strips at a distal end. The device is placed over an endoscope and the retracting device's flexible strips are expanded by a surgeon to retract tissue and retain the endoscope in position.

The novel tissue gripping device of the present invention obviates the disadvantages encountered in the prior art and provides improvements which are desirable for enhancing the retention properties of the cannula in the body wall. The device of the present invention provides a tissue gripping device which may work in concert with a cannula to retain the cannula in the body wall through the provision of articulated flexible members which extend outwardly to engage the body wall when in their extended position. The device includes means to positively retain the flexible members in an extended position so that the cannula is maintained in the body wall without the requirement of having surgical personnel hold the cannula in place.

SUMMARY OF THE INVENTION

The present invention provides a tissue gripping apparatus which comprises an outer sleeve concentrically positioned about an inner sleeve. A plurality of articulated arm members integral with the outer sleeve are positioned at a distal end of the outer sleeve. A hinge is located proximal a midpoint of each articulated arm. The articulated arm members further include means to manipulate the arm members to an extended position which situates an arm portion of each arm member at a location proximal the hinge in a substantially perpendicular orientation relative to the inner sleeve. The tissue gripping apparatus of the present invention further includes an improved mechanism for retaining the flexible member in an extended position and a non-extended position.

The present invention further provides a tissue gripping apparatus for use with a cannula. The tissue gripping apparatus of the present invention allows a surgeon to use the cannula in a hands-off manner. The tissue gripping apparatus comprises a cylindrical body portion concentrically supported about a cannula, where the body portion includes a flexible element at its distal end. The flexible element includes a plurality of articulated arm members each having a hinge located proximal of the midpoint of the arm member. The articulated arm member is manipulable between an elongated position in which the arm member is at rest and against the cannula and an extended deployed position which situates an arm portion proximal the hinge in a substantially perpendicular orientation relative to the cannula. The articulated arms are deployed by manipulating the cylindrical body portion of the device. The tissue gripping apparatus of the present invention provides enhanced retention of the surgical apparatus in a patient's body, and includes an improved mechanism for retaining the flexible member in an extended deployed position and a non-extended at rest position.

The present invention further provides a trocar assembly having an obturator and a cannula, in which the cannula of the trocar assembly comprises a tubular body portion having a flexible member concentrically positioned about the tubular body portion. The flexible member includes a plurality of articulated arm members each having a hinge located proximal of a midpoint of the arm member. The articulated arm member is manipulable between a non-extended at rest position and a deployed extended position which situates an arm portion proximal the hinge in a substantially perpendicular orientation relative to the cannula. Further, the cannula of the trocar assembly includes an improved mechanism for retaining the flexible member in an extended deployed position and a non-extended at rest position.

The present invention further includes a method for maintaining a tubular member such as a cannula within an opening in a body. The method comprises positioning an elongated tubular cannula in an incision where a cylindrical member is concentrically positioned about at least a portion of the cannula. The cylindrical member includes a flexible portion disposed at a distal end, and is manipulable between an extended deployed position and a non-extended at rest position by urging the cylindrical member distally to deploy the flexible portion to grip the body wall at the incision.

BRIEF DESCRIPTION OF THE DRAWINGS

The foregoing features of the present invention will become more readily apparent and may be better understood by referring to the following detailed description of an illustrative embodiment of the tissue gripping device for use with a trocar or cannula, taken in conjunction with the accompanying drawings, in which.

DETAILED DESCRIPTION OF THE PREFERRED EMBODIMENT

Figure 1:
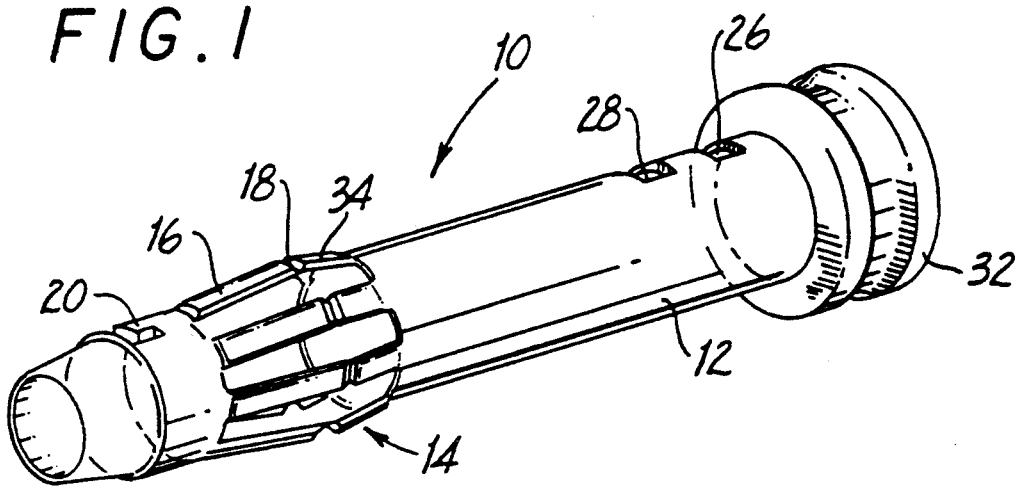
FIG. 1 is a perspective view illustrating a tissue gripping apparatus according to a first embodiment of the present invention.

Referring now in specific detail to the drawings, in which like reference numerals identify similar or identical elements, there is shown a tissue gripping apparatus 10 according to the present invention illustrated in FIGS. 1 through 4. As illustrated in FIG. 1, the tissue gripping apparatus 10 includes a cylindrical body portion 12, and a flexible element 14 having a plurality of substantially parallel arms 16. Each of the arms 16 have a hinge 18 located proximal to a midpoint of each respective arm, preferably each hinge 18 is substantially the same distance from the midpoint of the respective arms 16.

Figure 2:
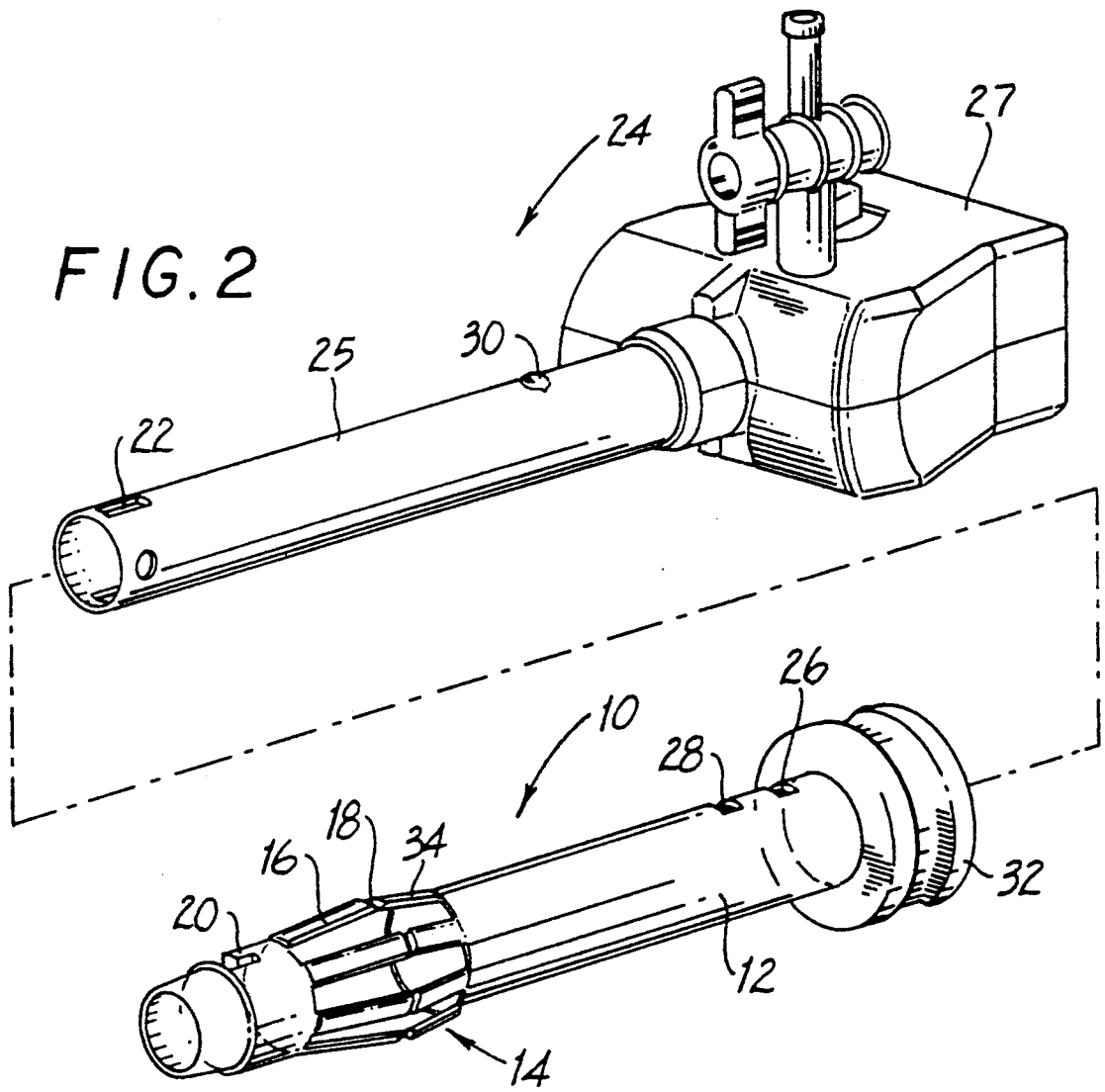
FIG. 2 is an exploded perspective view illustrating the tissue gripping apparatus according to a second embodiment of the present invention.

As seen in FIG. 2, the cylindrical body portion 12 further includes a resilient member 20 at its distal end comprising a tab which is designed to cooperate with a slot 22 in a cannula 24. The cannula includes a tubular body portion 25 and a valve body portion 27, as discussed below. The cylindrical body portion 12 of apparatus 10 further includes at least two slots 26 and 28 located at a proximal end of the body portion 12. Both slots 26, 28 are preferably at a proximal end of the body portion and are designed to cooperate with a substantially hemispheric surface 30 on the tubular body portion 25 of the cannula 24.

The cylindrical body portion 12, may be constructed, preferably, of a resiliently flexible material such as, for example, a polypropylene material, which is sufficiently resilient to flex over the outwardly directed hemispheric surface 30 on the tubular body portion 25 on the cannula 24. A gripping flange 32 is situated at a proximal end of the cylindrical body portion 12. The flange 32 allows a surgeon to easily move the cylindrical body portion 12 distally to deploy the articulated arms 16, as will be discussed below.

Figure 4:
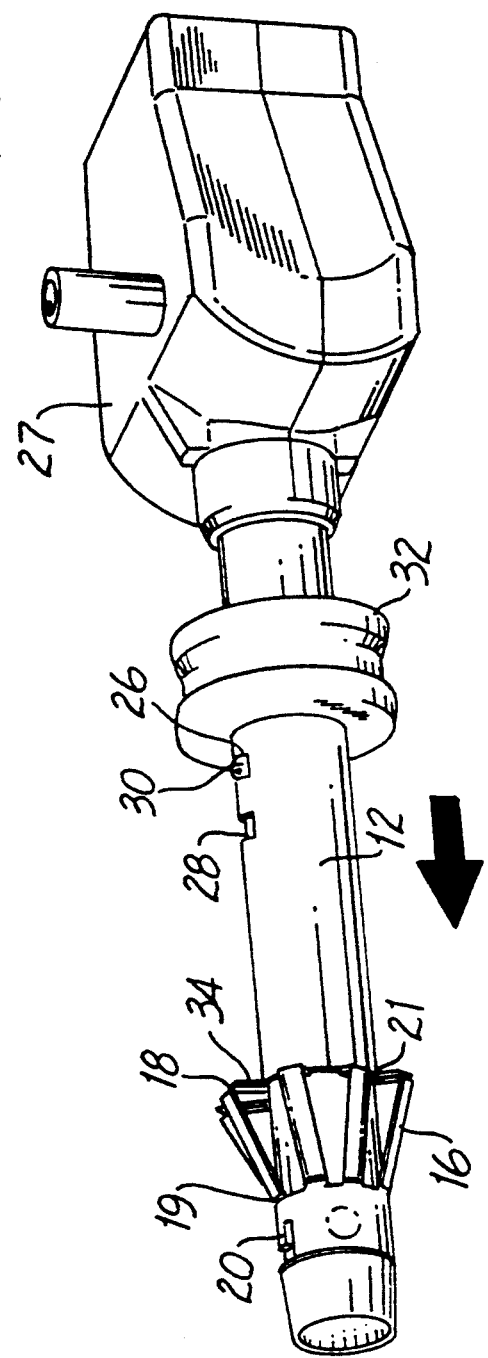
FIG. 4 is a perspective view illustrating the tissue gripping apparatus of FIG. 3 in a deployed position.

The location of hinge 18, proximal of the midpoint of each respective arm 16, results in an advantageous geometry when the articulated arms 16 are fully deployed when the cylindrical body portion 12 is advanced to its distal-most position, as described below. In particular, when fully deployed, the arm portions 34 on the proximal side of the hinge are shorter than the arm portions on the distal side of the hinge, and assume a substantially perpendicular orientation relative to the cannula, as shown in FIG. 4. This perpendicular orientation ensures optimal retention of the surgical apparatus in, for example, the abdomen by securingly engaging the inner wall of the abdominal cavity. Generally, from 3 to 12 arms are substantially evenly spaced around the circumference of the body portion 12, and preferably there are from 6 to 10 arms.

Referring to FIG. 2, the tissue gripping apparatus 10 of the present invention is used with a cannula 24 of a trocar assembly. The cannula 24 is provided with a substantially hemispheric surface 30 at the proximal end of its tubular member 25. The hemispheric surface 30 cooperates with the slots 26, 28 in the cylindrical body portion 12, such that the distal-most slot 28 cooperates with the hemispheric surface 30 when the tissue gripping apparatus 10 is non-deployed, and the proximal-most slot 26 cooperates with the hemispheric surface 30 when the tissue gripping apparatus 10 is fully deployed; that is, when the articulated arms 16 are in an extended position as shown in FIG. 4. The cannula further includes a slot 22 at its distal end designed to cooperate with the resilient tab member 20 at the distal end of the cylindrical body portion.

While it is preferred that the cannula be provided with the hemispheric surface 30 to engage slots 26 and 28 of the apparatus 10, the surface 30 may include an annular ring which would cooperate with an annular groove in apparatus 10, or may include an indentation in cannula body 25 and a corresponding protrusion in body portion 12.

Figure 3:
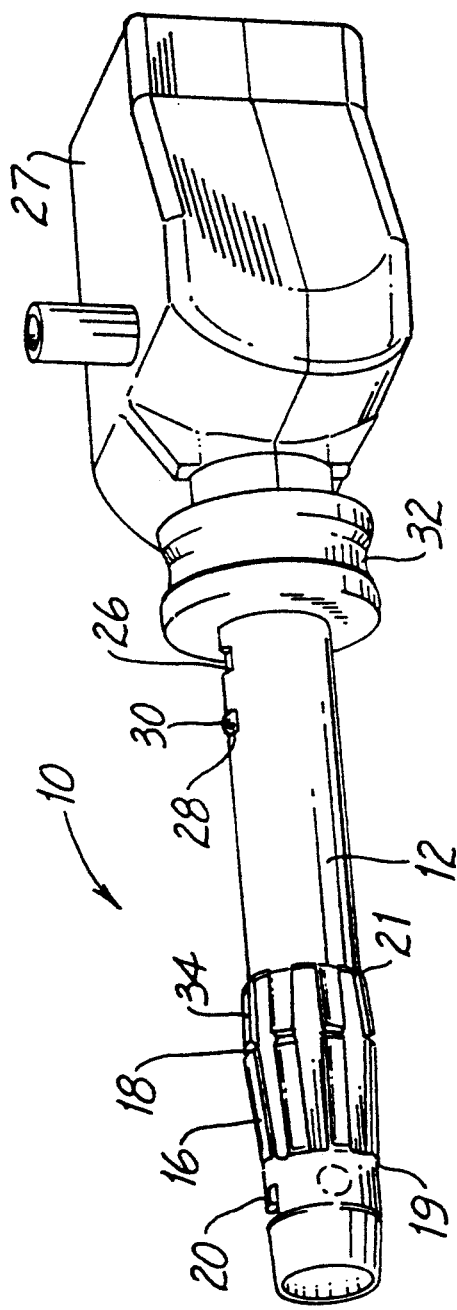
FIG. 3 is a perspective view illustrating the tissue gripping apparatus of FIG. 2 in an assembled condition in an at rest position.

Referring now to FIGS. 3 and 4, the cylindrical body portion 12 is shown fitted on the cannula 24 according to the present invention. As shown in FIG. 3, the articulated arms 16 of the cylindrical body portion 12 are in a non-engaged position and are positioned substantially in contact with the cannula as shown. In this position, the hemispheric surface 30 is cooperating with the distal-most slot 28 on the cylindrical body portion 12.

As seen in FIG. 4, the articulated arms 16 are in a deployed position, such that the arm portions 34 of the articulated arms 16 proximal the hinge 18 are in a substantially perpendicular orientation relative to the tubular portion 25 of the cannula 24. The proximal-most slot 26 in the cylindrical body portion 12 is cooperatingly engaged with hemispheric surface 30 to maintain the articulated arms 16 in the engaged position.

In operation, the surgeon uses the trocar assembly, having a pointed obturator (not shown) and inserts the trocar through the body wall of a patient. After the obturator is removed, the surgeon grasps the flanged surface 32 of gripping apparatus 10 and slides the cylindrical body portion 12 distally relative to the stationary cannula 24. The cylindrical body portion 12 material flexes over the hemispheric surface 30 to disengage surface 30 from slot 28, and the body portion 12 is moved until the hemispheric surface 30 enters the proximal-most slot 26. The articulated arms move outwardly as hinges 19 and 21 turn arms 16 and 34 away from body portion 12 through hinge 18, to a fully deployed position. The cooperation between the slots 26, 28 and the hemispheric surface 30 provides an improved mechanism for securing the articulated arms 16 in a deployed engaged and an at rest non-engaged position. The location of the hinge 18 on the articulated arms 16 allows the portion 34 of the articulated arms 16 proximal the hinge 18 to be substantially perpendicular to the tubular portion 25 of the cannula 24. The orientation of the articulated arms provides an enhanced means for restraining the cannula against the body wall in an incision in a patient's body.

Another embodiment of the tissue gripping apparatus 10 of the present invention may include a tube or a cannula having a movable outer sleeve cooperating with an inner sleeve that are not part of a trocar assembly. The inner and outer sleeves operate in a similar fashion to the cylindrical body portion 12 and the cannula 24 described above.

The present invention further comprises a method for gripping tissue which includes the steps of providing an elongated tubular cannula having a cylindrical member positioned about the cannula which includes a plurality of articulated arms. The articulated arms include a hinge positioned as described above. The cannula 24 and cylindrical member 12 cooperate as described above to provide an enhanced tissue gripping method.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A tissue gripping apparatus which comprises:
   an outer sleeve concentrically positioned about an inner sleeve;
   a plurality of articulated arm members integral with said outer sleeve and positioned adjacent a distal end thereof;
   at least one hinge being positioned proximal a midpoint of each of said articulated arm members, said hinge defining a proximal arm portion which is shorter than a distal arm portion;
   wherein said articulated arm members are manipulable between an at rest position and a deployed position.

2. A tissue gripping apparatus according to claim 1, wherein said arm members include a distal portion and a proximal portion joined by said hinge, said distal portion having a greater length than said proximal portion.

3. A tissue gripping apparatus according to claim 2, wherein said proximal arm is substantially perpendicular relative to said inner sleeve when said arm members are in said deployed position.

4. A tissue gripping apparatus which comprises:
   an outer sleeve concentrically positioned about an inner sleeve, and slidable between an at rest position and a deployed position;
   a flexible member being disposed at a distal end of said outer sleeve; and
   at least two slots in a proximal end of said outer sleeve and engageable with at least one cooperating raised member on a proximal end of said inner sleeve for retaining said outer sleeve in said at rest position and said deployed position relative to said inner sleeve.

5. A tissue gripping apparatus according to claim 4, wherein said cooperating raised member includes a hemispheric surface on said inner sleeve.

6. A tissue gripping apparatus according to claim 5, wherein said hemispheric surface is integral with said inner sleeve.

7. A tissue gripping apparatus according to claim 5, wherein said hemispheric surface is coupable with said inner sleeve.

8. A tissue gripping apparatus according to claim 4, wherein said outer sleeve includes a gripping flange member disposed at a proximal end thereof.

9. A tissue gripping apparatus according to claim 4, wherein said flange has a diameter greater than a diameter of said outer sleeve.

10. A tissue gripping apparatus which comprises:
    an outer sleeve slidably and concentrically positioned about an inner sleeve; a plurality of articulated arms integral with said outer sleeve and positioned adjacent a distal end thereof;
    a hinge positioned proximal of a midpoint of each of said articulated arms, said hinges demarcating proximal arm portions and distal arm portions such that said proximal arm portions are shorter in length than said distal arm portions, said hinges positioning said articulated arms in an extended and a non-extended position upon sliding said outer sleeve in relation to said inner sleeve.

11. A tissue gripping apparatus according to claim 10, wherein said proximal portions of said articulated arms are positioned substantially perpendicular to said inner sleeve when said arms are in said deployed position.

12. A tissue gripping apparatus according to claim 10, wherein said outer sleeve and said articulated arms are integrally molded of a plastic material.

13. A tissue gripping apparatus according to claim 10, wherein said articulated arms are constructed of a shape memory material.

14. A tissue gripping apparatus for use with a cannula, which comprises:
a cylindrical body portion slidably positioned about said cannula;
a plurality of articulated arms integral with said body portion and being disposed at a distal end of said body portion; and
at least one hinge being positioned proximal of a midpoint of each of said articulated arms, said hinge demarcating proximal arm portions and distal arm portion such that said proximal arm portions are shorter in length than said distal arm portions, said hinges positioning said articulated arms in an extended and a non-extended position upon sliding of body portion in relation to said cannula.

15. A tissue gripping apparatus according to claim 14, wherein said plurality of articulated arms include between 3 arms and 12 arms substantially evenly spaced and circumferencially about said cylindrical body portion.

16. A tissue gripping apparatus according to claim 15 wherein said plurality of articulated arms include between 6 arms and 10 arms.

17. A tissue gripping apparatus according to claim 14, wherein said proximal portions of said articulated arms are positioned substantially perpendicular to said inner sleeve when said arms are in said deployed position.

18. A tissue gripping apparatus according to claim 14, further comprising means to retain said body portion in said extended position, said retaining means including a pair of slots in said body portion and a cooperating raised hemispheric surface on said cannula.

19. A tissue gripping apparatus according to claim 14, wherein said cylindrical body portion includes a flange member disposed at a proximal end thereof.

20. A tissue gripping apparatus according to claim 14, wherein said body portion and said articulated arms are integrally molded of a plastic material.

21. A tissue gripping apparatus according to claim 14, wherein said articulated arms are constructed of a shape memory material.

22. A cannula comprising:
a tubular body portion;
an outer sleeve slidably positioned about said tubular body portion;
a plurality of articulated arm members positioned at a distal end of said outer sleeve, and a hinge positioned proximal of a midpoint of each of said arm, said articulated arms being manipulable between an extended position and a non-extended position, such that a portion of each arm proximal each of said hinges is positioned perpendicular relative to said inner sleeve when said arms are in said extended position; and
means for retaining said articulated arms in said extended position and said non-extended position.

23. A cannula according to claim 22, wherein said articulated arms are integral with said outer sleeve.

24. A cannula according to claim 22, wherein said articulated arms and said outer sleeve are integrally molded of a plastic material.

25. A cannula according to claim 22, wherein said retaining means comprises at least two slots on said outer sleeve engageable with a tab member on said tubular body portion, said slots and tabs being positioned at a proximal end of said cannula.

26. A cannula according to claim 25, wherein said tab member comprises a hemispheric surface integral with said tubular body portion.

27. A cannula according to claim 22, wherein said outer sleeve includes a flange member disposed at a proximal end thereof for gripping said outer sleeve to move said outer sleeve between said extended and said non-extended positions.

28. In a trocar assembly including an obturator and a cannula, said cannula having an elongated cylindrical body having an opening at a proximal end for receiving said obturator and an opening at a distal end; the improvement which comprises:
an outer sleeve slidably positioned about said cannula for gripping tissue of a patient at an incision upon insertion of said cannula into said patient;
a plurality of articulated arm members integral with said outer sleeve positioned at a distal end thereof; and
at least one hinge proximal of a midpoint of each of said articulated arm members said hinge defining a proximal arm portion which is shorter than a distal arm portion;
wherein said articulated arm members are manipulable about said hinges between an extended position and a non-extended position upon sliding said outer sleeve in relation to said cannula.

29. A trocar assembly according to claim 28, wherein each of said articulated arms include an arm portion proximal the hinge which is positioned substantially perpendicular relative to said cannula in said extended position.

30. A trocar assembly according to claim 29, further comprising means for retaining said outer sleeve in said extended and said non-extended position.

31. In a trocar assembly including an obturator and a cannula, the improvement which comprises:
an outer sleeve slidably and concentrically positioned about said cannula;
a plurality of articulated members each having a hinge proximal to a midpoint of said articulated members for positioning said articulated arms between an extended and non-extended position;
at least two slots in said outer sleeve and engageable with at least one cooperating raised hemispheric member integral with said cannula for retaining said outer sleeve in said extended and said non-extended positions relative to said cannula; and
a flange member disposed at a proximal end of said outer sleeve having a diameter greater than a diameter of said outer sleeve for moving said outer sleeve between said extended and said non-extended position.

32. A trocar assembly according to claim 31, wherein said articulated arm members are extended in a generally radially outwardly direction from said outer sleeve when said outer sleeve is advanced distally, and said articulated arms are retractable to said non-extended position in a generally radially inwardly direction when said outer sleeve is moved proximally.

33. A method for restraining a cannula within an opening in a body comprising:

inserting said cannula into said opening in said body, said cannula having a raised member extending at a proximal end from an outer surface thereof;

said cannula including a cylindrical sleeve member slidably positioned about said cannula, said cylindrical sleeve member having a plurality of articulated arm members disposed at said distal end thereof, said cylindrical sleeve member further including means for cooperatively receiving said raised portion extending from said cannula to retain said sleeve member in an extended and non-extended position; and advancing said cylindrical sleeve member distally to move said articulated arm members to said extended position to maintain said cannula in said body opening;

wherein said arm members include a hinge proximal of a midpoint of each of said articulated arms, said hinge demarcating proximal arm portions and distal arm portions, such that said proximal arm portions are shorter than said distal arm portions, and such that said proximal arm portions are substantially perpendicular to said cannula when said sleeve member is in said extended position.

* * * * *